US012004984B1

(12) United States Patent
Solotoff

(10) Patent No.: US 12,004,984 B1
(45) Date of Patent: Jun. 11, 2024

(54) ANKLE STABILIZER BRACE

(71) Applicant: PREFERRED PRESCRIPTION, INC., Hollywood, FL (US)

(72) Inventor: Brandon Solotoff, Boca Raton, FL (US)

(73) Assignee: Preferred Prescription INC., Hollywood, FL (US)

(*) Notice: Subject to any disclaimer, the term of this patent is extended or adjusted under 35 U.S.C. 154(b) by 81 days.

(21) Appl. No.: 17/083,635

(22) Filed: Oct. 29, 2020

Related U.S. Application Data

(60) Provisional application No. 62/930,660, filed on Nov. 5, 2019.

(51) Int. Cl.
*A61F 5/01* (2006.01)

(52) U.S. Cl.
CPC .................. *A61F 5/0111* (2013.01)

(58) Field of Classification Search
CPC ........ A61F 5/01; A61F 5/0102; A61F 5/0104; A61F 5/0106; A61F 5/0111; A61F 5/0113; A61F 5/0123; A61F 5/0127; A61F 5/00; A61F 5/04; A61F 5/05; A61F 5/0585; A61F 2005/0165; A61F 13/06; A61F 13/064; A61F 13/065; A61F 13/066; A61F 13/08; A43B 7/20; A43B 23/07
See application file for complete search history.

(56) References Cited

U.S. PATENT DOCUMENTS 2,573,791 A 11/1951 Howells
2,715,315 A 8/1955 Giardini
(Continued)

FOREIGN PATENT DOCUMENTS

CN 102711683 B 10/2012
CN 204971762 U 1/2016
(Continued)

OTHER PUBLICATIONS

Lijing Wang, Martin Felder, Jackie Cai; "Study of Properties of Medical Compression Fabrics," J. of Fiber Bioengineering & Informatics, Global Science Press, p. 15-22 (2011).
(Continued)

*Primary Examiner* — Ophelia A Hawthorne
*Assistant Examiner* — Gina McCarthy
(74) *Attorney, Agent, or Firm* — Thomas A. O'Rourke; James Bongiorno; O'Rourke IP Law PLLC

(57) ABSTRACT

An ankle brace includes a wrap, lateral and medial stays, and first and second strap portions (e.g., a single unitary strap) secured to the wrap. A first wrap portion envelops the foot, and a second wrap portion envelops a portion of the lower leg. The lateral and medial stays have question-mark-shaped peripheries, and extend along portions of the lower leg, the ankle, and lateral and medial portions of the foot, respectively. The first and second strap portions wrap around a top of the foot in first and second directions, respectively, around the back of the leg, and releasably secure to lateral and medial sides of the wrap. Each stay overlaid by the first and second strap portions at three locations to redundantly secure each stay to the wrap. The lateral and medial stays may be contoured according to the lateral and medial sides of the foot, ankle, and lower leg.

11 Claims, 15 Drawing Sheets

(56) References Cited

U.S. PATENT DOCUMENTS

| | | | |
|---|---|---|---|
| 3,073,305 A * | 1/1963 | Biggs, Jr. | A61F 5/0111 602/65 |
| 3,175,558 A | 3/1965 | Caillouette | |
| 3,327,703 A | 6/1967 | Gamm | |
| 3,900,035 A | 8/1975 | Welch | |
| 4,055,188 A | 10/1977 | Pelton | |
| 4,092,982 A | 6/1978 | Salem | |
| 4,625,729 A | 12/1986 | Roney | |
| 4,669,476 A | 6/1987 | Gordon | |
| 4,726,126 A * | 2/1988 | Bernhard | A43B 7/20 36/89 |
| 4,800,867 A | 1/1989 | Owens | |
| 4,844,094 A | 7/1989 | Grim | |
| 4,938,222 A | 7/1990 | Bier | |
| 4,964,402 A | 10/1990 | Grim | |
| 5,000,176 A | 3/1991 | Daniel | |
| 5,111,810 A | 5/1992 | Fortney | |
| 5,165,402 A | 11/1992 | McCoy | |
| 5,199,941 A | 4/1993 | Makinen | |
| 5,393,303 A * | 2/1995 | Shiono | A61F 5/0111 602/23 |
| 5,407,421 A | 4/1995 | Goldsmith | |
| 5,415,624 A | 5/1995 | Williams | |
| 5,483,703 A | 1/1996 | Williams | |
| 5,496,358 A | 3/1996 | Rosenwald | |
| 5,501,659 A | 3/1996 | Morris | |
| 5,873,903 A | 2/1999 | Garcia | |
| 5,935,157 A | 8/1999 | Harmon | |
| 5,957,871 A * | 9/1999 | Darcey | A61F 5/0111 602/8 |
| 6,001,122 A | 12/1999 | Lyles | |
| 6,173,589 B1 | 1/2001 | Hayes | |
| 6,440,159 B1 | 8/2002 | Edwards | |
| 6,582,383 B2 | 6/2003 | Horning | |
| 6,589,272 B1 | 7/2003 | Sheikh | |
| 6,598,235 B2 | 7/2003 | Bulla | |
| 6,617,485 B2 | 9/2003 | Herzberg | |
| 6,652,474 B1 | 11/2003 | Quinn | |
| 6,656,210 B1 | 12/2003 | Plewes | |
| 6,929,617 B2 | 8/2005 | McCormick | |
| 6,973,742 B2 | 12/2005 | Gordon | |
| 7,060,086 B2 | 6/2006 | Wilson | |
| 7,481,786 B2 | 1/2009 | Flick | |
| 8,007,454 B1 * | 8/2011 | Zerr | A61F 5/0111 602/23 |
| 8,231,816 B2 | 7/2012 | Kingsford | |
| 8,454,545 B1 * | 6/2013 | Weber | A61F 5/0111 602/65 |
| 8,603,151 B2 | 12/2013 | Latham | |
| 8,986,235 B2 | 3/2015 | Weaver | |
| 9,402,437 B2 * | 8/2016 | Berns | A43B 23/07 |
| D818,138 S | 5/2018 | Nicosia | |
| 10,555,863 B2 | 2/2020 | Hall | |
| 2003/0195439 A1 | 10/2003 | Caselnova | |
| 2004/0019309 A1 * | 1/2004 | Nelson | A61F 5/0111 602/65 |
| 2004/0158283 A1 | 8/2004 | Shook | |
| 2007/0100264 A1 | 5/2007 | Hanson | |
| 2008/0066272 A1 | 3/2008 | Hammerslag | |
| 2008/0082034 A1 | 4/2008 | Wilkerson | |
| 2009/0005717 A1 * | 1/2009 | Brzank | A61F 5/0111 602/65 |
| 2009/0076428 A1 * | 3/2009 | Kay | A61F 5/0111 602/27 |
| 2009/0125086 A1 | 5/2009 | Juta | |
| 2011/0196276 A1 | 8/2011 | Kuhn | |
| 2011/0224762 A1 | 9/2011 | Gruber | |
| 2012/0023782 A1 | 2/2012 | Zaragosa | |
| 2012/0029404 A1 | 2/2012 | Weaver | |
| 2014/0309572 A1 | 10/2014 | Heyd | |
| 2014/0316314 A1 | 10/2014 | Schubert | |
| 2015/0119775 A1 | 4/2015 | Gildersleeve | |
| 2016/0095735 A1 * | 4/2016 | Wenger | A61F 5/0113 602/28 |
| 2016/0228298 A1 | 8/2016 | Geller | |
| 2017/0367868 A1 | 12/2017 | Ducharme | |
| 2018/0055686 A1 | 3/2018 | Munoz | |
| 2020/0100928 A1 * | 4/2020 | Best | A61F 5/0111 |

FOREIGN PATENT DOCUMENTS

| | | |
|---|---|---|
| DE | 102006016988 A1 | 10/2007 |
| DE | 102015000783 A1 | 7/2016 |
| EP | 1517656 B1 | 2/2008 |
| KR | 101553243 B1 | 9/2015 |
| WO | WO2006048619 A1 | 5/2006 |
| WO | WO2008077112 A2 | 6/2008 |
| WO | WO2011140487 A2 | 11/2011 |

OTHER PUBLICATIONS

Ying Xiong, Xiaoming Tao; "Compression Garments for Medical Therapy and Sports," Polymers, vol. 10, No. 663, 3-19, Jun. 14, 2018.

Li Z, Malengier B, Vasile S, Cools J, Van Langenhove L; "From 3d Scan To Body Pressure Of Compression Garments," AUTEX2019—19th World Textile Conf., Jun. 11-15, 2019, Beljium.

Hugo Partsch, "Physics of Compression," Published by Guset User, Nov. 24, 2015.

Dennis-Peter Born, et al., "Bringing Light Into the Dark: Effects of Compression Clothing on Performance & Recovery," Int'l J. of Sports Phys. & Performance, 8:4-18 (2013).

Prawit Janwantanakul, "Cold pack/skin interface temperature during ice treatment with various levels of compression," Physiotherapy, 2006;92:254-259.

\* cited by examiner

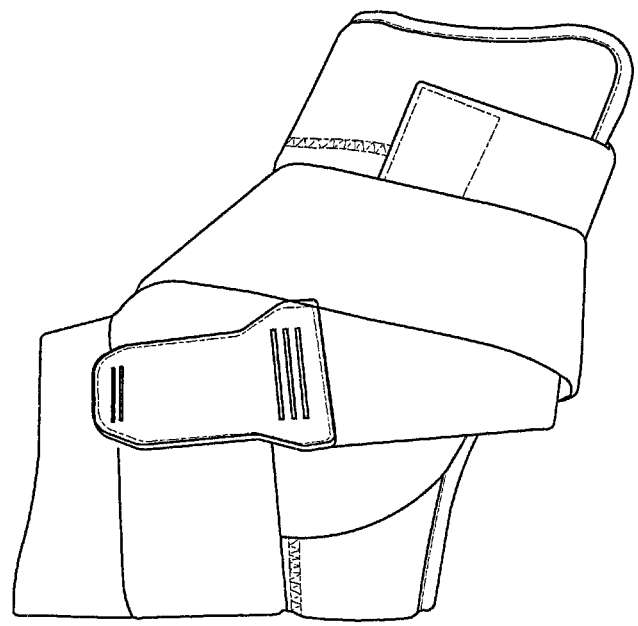
FIG.15
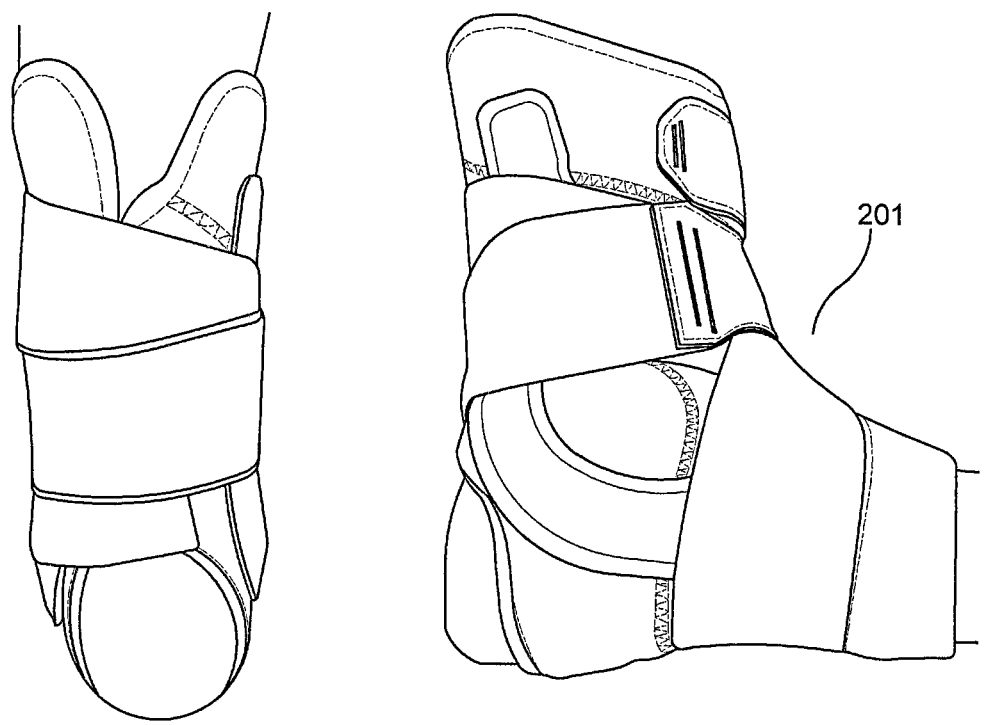
FIG.16
FIG.17

ANKLE STABILIZER BRACE

CROSS REFERENCES TO RELATED APPLICATIONS

This application claims priority on U.S. Provisional Application Ser. No. 62/930,660, filed on Nov. 5, 2019, the disclosures of which are incorporated herein by reference.

FIELD OF THE INVENTION

The subject technology relates generally to orthopedic braces, and more specifically to a brace particularly configured to stabilize the wearer's ankle.

BACKGROUND OF THE INVENTION

For many years athletes taped their ankles to provide support and to reduce the risk and severity of ankle injuries. During the 1990s ankle braces were more often being worn by athletes, because they were easy to put on, and less expensive than having a trainer carefully tape the person's ankle. Ankle braces are now typically worn by athletes and non-athletes to both prevent an injury from occurring, and to also prevent aggravating and worsening of an existing or recently healed injury.

There are many different types of ankle braces, generally being either a pull-on brace that tends to provide less support, or a lace-up or strap-type brace that can be tightened to different degrees about the wearer's foot, ankle, and/or leg.

Ankle braces are typically configured to stop eversion and/or inversion, because traumatic injury often occurs with those motions (see U.S. Pat. No. 5,944,678 to Hubbard; U.S. Pat. No. 4,844,094 to Grim; U.S. Pat. No. 5,056,509 to Swearington; and U.S. Pat. No. 6,929,617 to McCormick).

Inversion is where a person (often an athlete) plants his/her foot to resist a large lateral force and the person's foot rolls onto its lateral surface (i.e., the persons stands on the outside edge of the foot) while the lower leg (or tibia) remains relatively upright, which stretches the outer ligaments too far, causing pain on the outside of the ankle. Inversion can result in a soft-tissue injury (e.g., a sprain) and also bone fractures (e.g., a Weber fracture—a fracture of the distal fibula).

Eversion is where the athlete's foot rolls onto its medial surface (i.e., the person stands on the inside edge of the foot), which stretches the inner ligaments too far, causing pain on the inside of the ankle.

The ankle stabilizer brace disclosed herein, while providing support to prevent inversion and eversion, is additionally configured to prevent injuries from excessive or maximal dorsiflexion motion known as anterior ankle impingement, where the foot and shin move towards one another (i.e., extension of the ankle/foot so that the foot points up toward the leg). Excessive dorsiflexion motion creates compressive forces on the bony or soft tissue structures at the front of the ankle joint causing pain. If the compressive forces exceed the capacity of the person's ankle, damage and inflammation will occur.

The ankle stabilizer brace disclosed herein is additionally configured to prevent injuries from excessive or maximal plantar flexion motion, where the foot and shin move away from each other (i.e., the foot points down and away from the leg).

The ankle stabilizer brace disclosed herein is additionally configured to prevent injuries from supination (where weight is placed on the outside of the foot while walking or running) and pronation (where the person shifts his/her weight from the heel to the forefoot), each of which may result in pain.

It is noted that citing herein of any patents, published patent applications, and non-patent literature is not an admission as to any of those references constituting prior art with respect to the herein disclosed apparatus.

OBJECTS OF THE INVENTION

It is an object of the invention to provide a brace that is configured to support a wearer's ankle.

It is another object of the invention to provide a brace that is configured to prevent injury to a wearer's ankle.

It is a further object of the invention to provide a brace that is configured to protect a wearer's ankle while recovering from an ankle injury.

It is another object of the invention to provide a brace that supports the wearer's ankle to prevent injury thereto resulting from inversion.

It is also an object of the invention to provide a brace that supports the wearer's ankle to prevent injury thereto resulting from eversion.

It is a further object of the invention to provide a brace that supports the wearer's ankle to prevent injury thereto resulting from excessive or maximal dorsiflexion motion.

It is another object of the invention to provide a brace that supports the wearer's ankle to prevent injury thereto resulting from excessive or maximal plantar flexion.

It is also an object of the invention to provide a brace that supports the wearer's ankle to prevent injury thereto resulting from supination.

It is a further object of the invention to provide a brace that supports the wearer's ankle to prevent injury thereto resulting from pronation.

Further objects and advantages of the invention will become apparent from the following description and claims, and from the accompanying drawings.

BRIEF DESCRIPTION OF THE DRAWINGS

The description of the various example embodiments is explained in conjunction with appended drawings, in which:

FIG. 15 illustrates a left side view of another embodiment of an ankle stabilizer brace;

FIG. 16 is a rear view of the ankle stabilizer brace of FIG. 15;

FIG. 17 is a right view of the ankle stabilizer brace of FIG. 15;

FIG. 22 is a flat pattern of the ankle stabilizer brace of FIG. 15, being of the circumferential portion and the first and second cuff portions that are respectively configured to be received upon the foot of the wearer and secured about the wearer's leg above the ankle;

FIG. 23 is a side view of the outer side of a person's leg and foot, showing the outer stay of the ankle stabilizer brace of FIG. 15 positioned thereon, and being shaped with contours to conform to the contour of the outside of the leg at the regions of contact therebetween;

FIG. 24 is a side view of the inner side of a person's leg and foot, showing the inner stay of the ankle stabilizer brace of FIG. 15 positioned thereon, and being shaped with contours to conform to the contour of the inside of the leg at the regions of contact therebetween;

FIG. 25 is a side perspective view of the inner side of the person's leg and foot, and the inner stay as shown in FIG. 24;

FIG. 26 is a rear view of the inner side of the person's leg and foot and the inner stay, as shown in FIG. 24;

FIG. 27 is the rear view of FIG. 26 shown enlarged;

FIG. 28 is a side view of the inner stay shown in FIG. 27;

FIG. 29 is a bottom perspective view of the inner side of the person's leg and foot and the inner stay, as shown in FIG. 24;

FIG. 30 is a bottom view of the inner side of the person's leg and foot and of the inner stay, as shown in FIG. 24;

FIG. 31 is a bottom view of the inner stay shown in FIG. 30;

FIG. 32 is a rear view of another embodiment of an outer stay;

FIG. 33 is a rear view of another embodiment of an inner stay;

FIG. 34 is a side view of the inner stay of FIG. 33; and

FIG. 35 shows positioning of the inner and outer stays with respect to the flat pattern of FIG. 22.

DETAILED DESCRIPTION OF THE INVENTION

Figure 1:
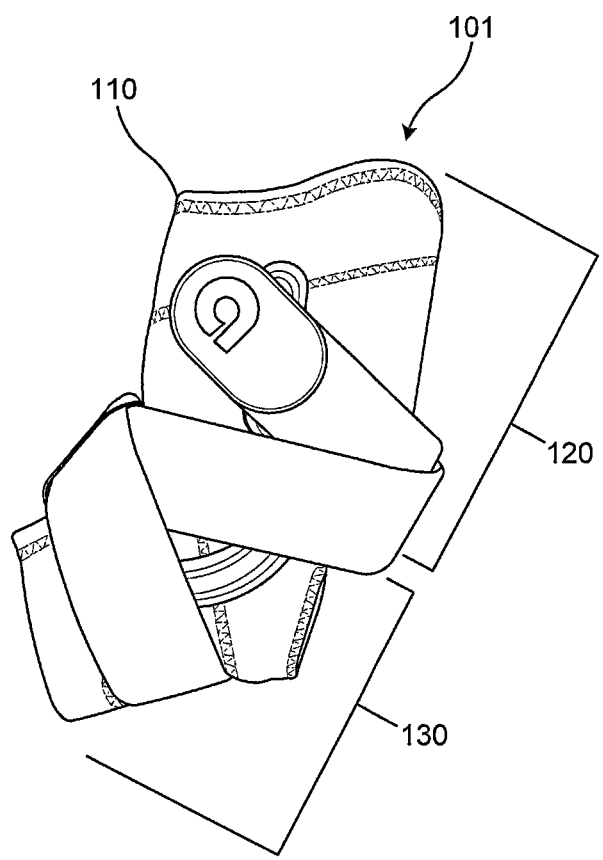
FIG. 1 illustrates a left side view of a first embodiment of an ankle stabilizer brace disclosed herein.
Figure 2:
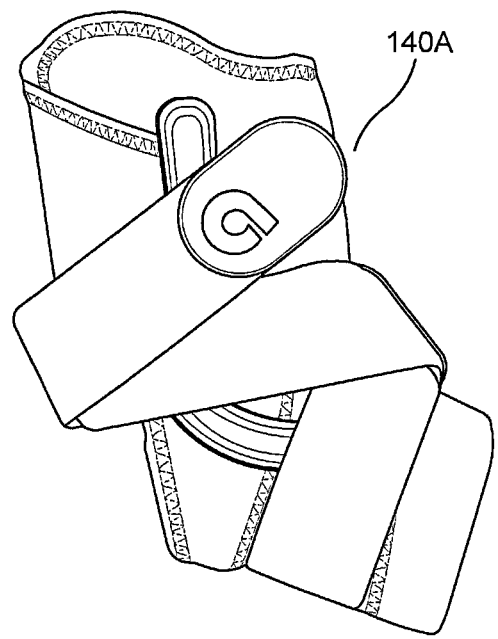
FIG. 2 illustrates a right side view of the ankle stabilizer brace of FIG. 1.
Figure 3:
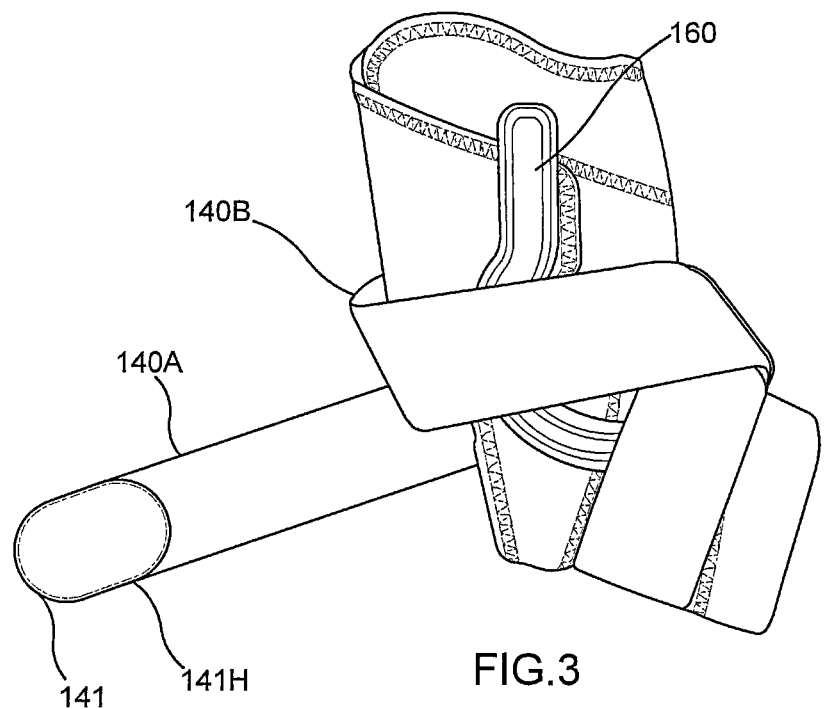
FIG. 3 is the right side view of FIG. 2, but showing an end of a first strap portion after being detached from the right side of the ankle stabilizer brace.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculatora/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit—i.e., loose running, free running, easy running, close running, and sliding (e.g., for a 0.1250 inch shaft diameter the opening may be 0.1285 inches for a close running fit, and may be 0.1360 inches for a free running fit; for a 0.5000 inch diameter shaft the opening may be 0.5156 inches for a close running fit and may be 0.5312 inches for a free running fit). Other clearance amounts are used for other clearance types. See "Engineering Fit" at: https://en.wikipediaorg/wiki/Engineering_fit; and "Three General Types of Fit," available at www.mm-to.org/dclark/Reports/Encoder%20Upgrade/fittolerences%20%5BRead-Only%5D.pdf.

Figure 10:
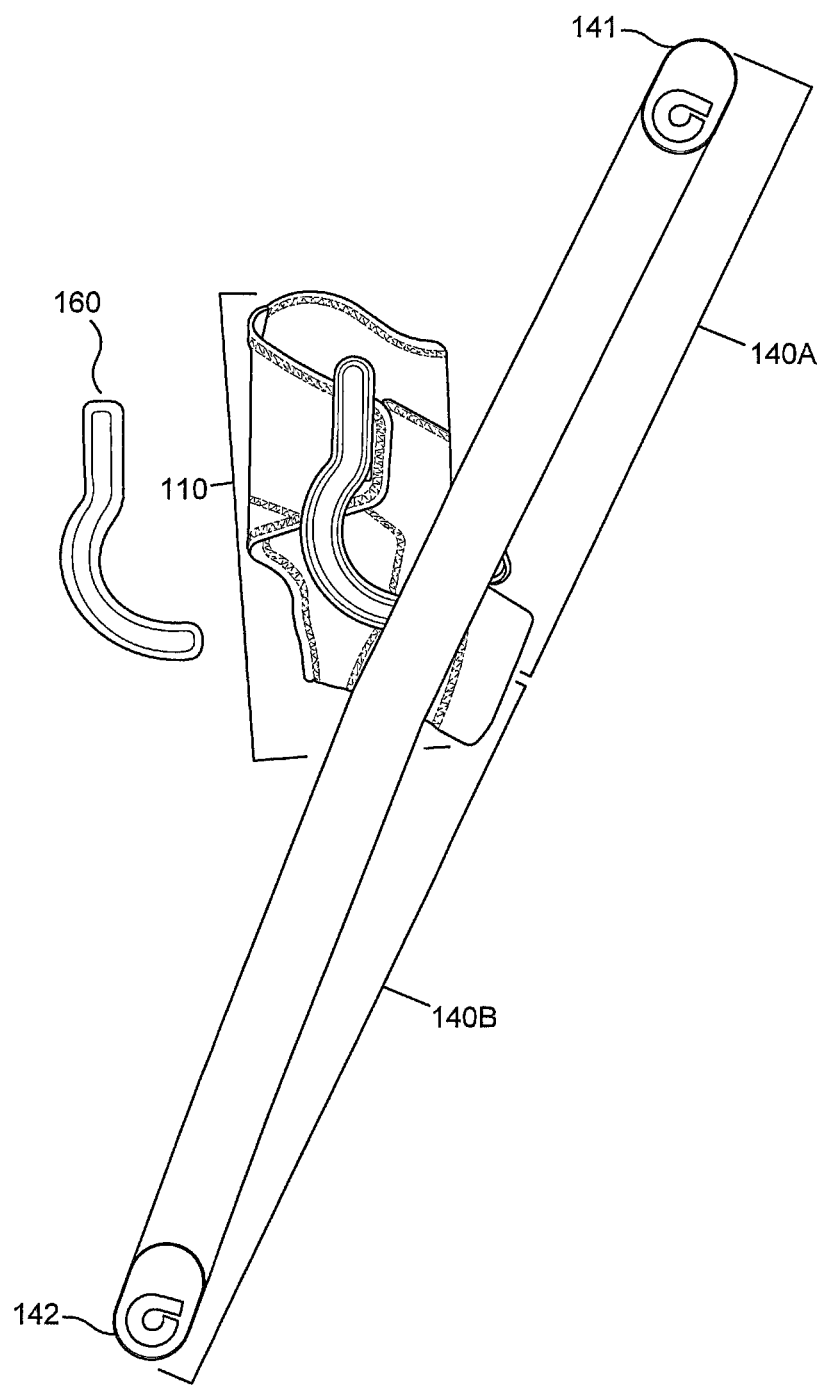
FIG. 10 is the ankle stabilizer brace of FIG. 9, but as seen from the right side.
Figure 11:
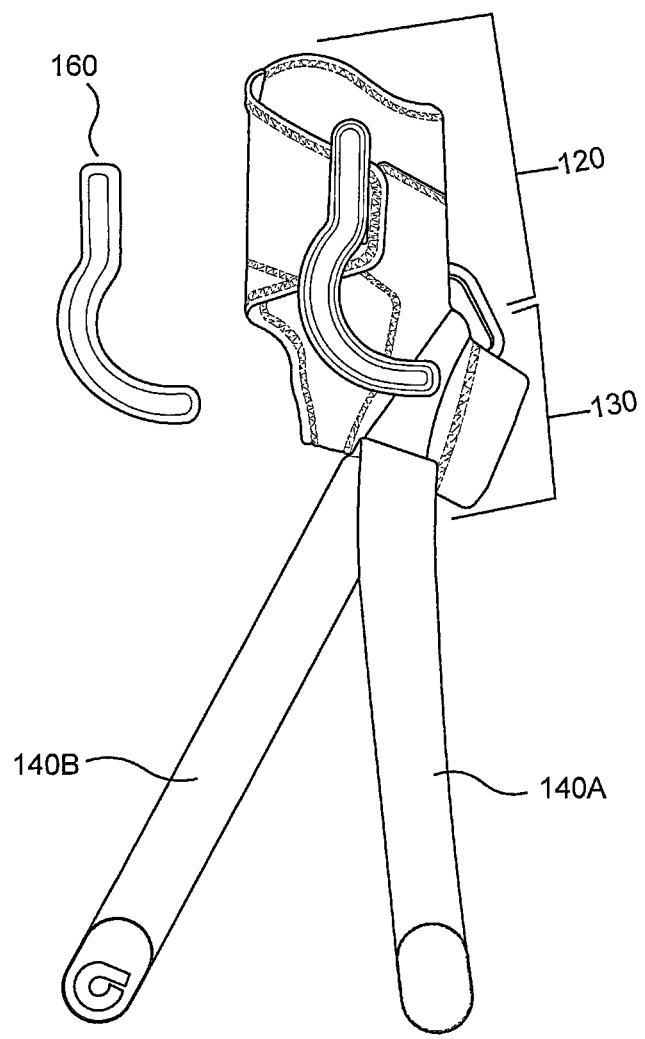
FIG. 11 is a right side view of the ankle stabilizer brace of FIG. 10, but showing the first strap portion after being removed from the support loop and unwound away from the right side of the ankle stabilizer brace, and stretched outwardly therefrom to completely expose a second particularly shaped stay.

FIGS. 1-14 illustrate a stabilizer brace 101 that is particularly configured to support and protect an ankle of a wearer against injury by limiting motion between a foot and lower leg of the wearer. The ankle stabilizer brace 101 may be formed of a wrap 110, a single long strap 140 (or two smaller straps), a medial stay 160, and a lateral stay 170 (see FIG. 10 and FIG. 12).

The wrap 110 may be formed of a leg portion 120 and a foot portion 130 (see FIG. 1 and FIG. 11), which leg and foot portions may be formed as a unitary part and may generally envelop the ankle and surrounding regions. The wrap 110 may be formed into various different sizes for different users, which sizes may mimic the different shoe sizes worn by most people (e.g., sizes 5, 5½, 6, 6½, 7, 7½, 8, 8½, 9, 9½, 10, 10½, 11, 11½, 12, 12½, etc.), to provide adequate support for each wearer.

The wrap 110 may be formed of any suitable material that is flexible. In one embodiment the wrap may be formed of a flexible material that is substantially inelastic (i.e., having little or no elongation capability). In another embodiment the wrap may be formed of a flexible material that is slightly elastic (e.g., having a maximum percent elongation of 2% to 5% in one embodiment, or 5% to 10% in another embodiment, or 10% to 15% in yet another embodiment, or 15% to 20% in a further embodiment, or any combination of such ranges or other elongation amounts in other embodiments.). Utilizing a material for the wrap 110 that has at least a small amount elasticity (i.e., 2% to 5% or 5% to 10%) may be preferable as it may permit suitable placement of the brace on a wearer whose feet may be between the standard foot sizes.

The foot portion 130 may comprise a tube-like shape configured to envelop at least a portion of the foot of the wearer between the toes and the heel (i.e., it may extend circumferentially around the foot, extending continuously around the top, the medial side, the bottom, the lateral side and back to the top of the foot). In one embodiment, foot portion 130 may be configured to only envelop a portion of the foot between the toes and the heel, leaving all of the toes and a portion of the heel exposed when the brace is being worn. As the periphery of the foot tends to increase in moving from the toes toward the ankle, the foot portion 130, while being flexible, may when expanded out may be shaped somewhat like a conical frustum rather than being cylindrical.

The leg portion 120 may be configured to be secured about the wearer's leg above the ankle. The leg portion 120 may be formed similar to the cuff of blood pressure measurement equipment—a sphygmomanometer (but without being inflatable), as it may be split (see FIG. 13 and FIG. 14) to form a first end 121 and a second end 122, and where the first end 121 may extend to include a flap portion 123 that may be of sufficient length to overlap over and beyond the first end 121 (see FIG. 12) when wrapped about the wearer's foot. The outside of the second end 122 of the leg portion 120 may have a patch of hook or loop material secured thereto, while the inside of the flap portion 123 may have a patch of the other of the hook and loop materials fixedly secured thereto (i.e., patches of hook and loop fastening materials—a descriptive name-sold under the trademark VELCRO). In one embodiment, the wrap 110 may be formed to have at least a portion of the sides of the exterior of the leg portion 120 and the foot portion 130 be formed of the loop material, while the inside of the flap may have the patch or patches of the hook material secured thereto, or be integrally formed therewith.

The medial stay 160 and lateral stay 170 are each formed to have a selectively-shaped periphery configured to extend along portions of the lower leg, ankle and foot of the wearer, and are configured for respective attachment to medial and lateral sides of the wrap 110 to inhibit relative motion between the foot and lower leg of the wearer. Each of the medial stay 160 and lateral stay 170 may be constructed of a suitable material to be rigid about one axis (i.e., an axis perpendicular to the page of FIG. 14) due to its peripheral shape, while exhibiting a minimal amount of flex about the other two axes owing to its thickness.

Each of the medial stay 160 and lateral stay 170 may be formed to be substantially flat, and may have a selectively shaped periphery so that it may extend along a portion of the lower leg (i.e., being centered upon the tibia and fibula bones—see FIG. 24), and extend around the back and lower sides of the ankle, and along a portion of the foot of the wearer to form a question-mark-shaped periphery.

Figure 14:
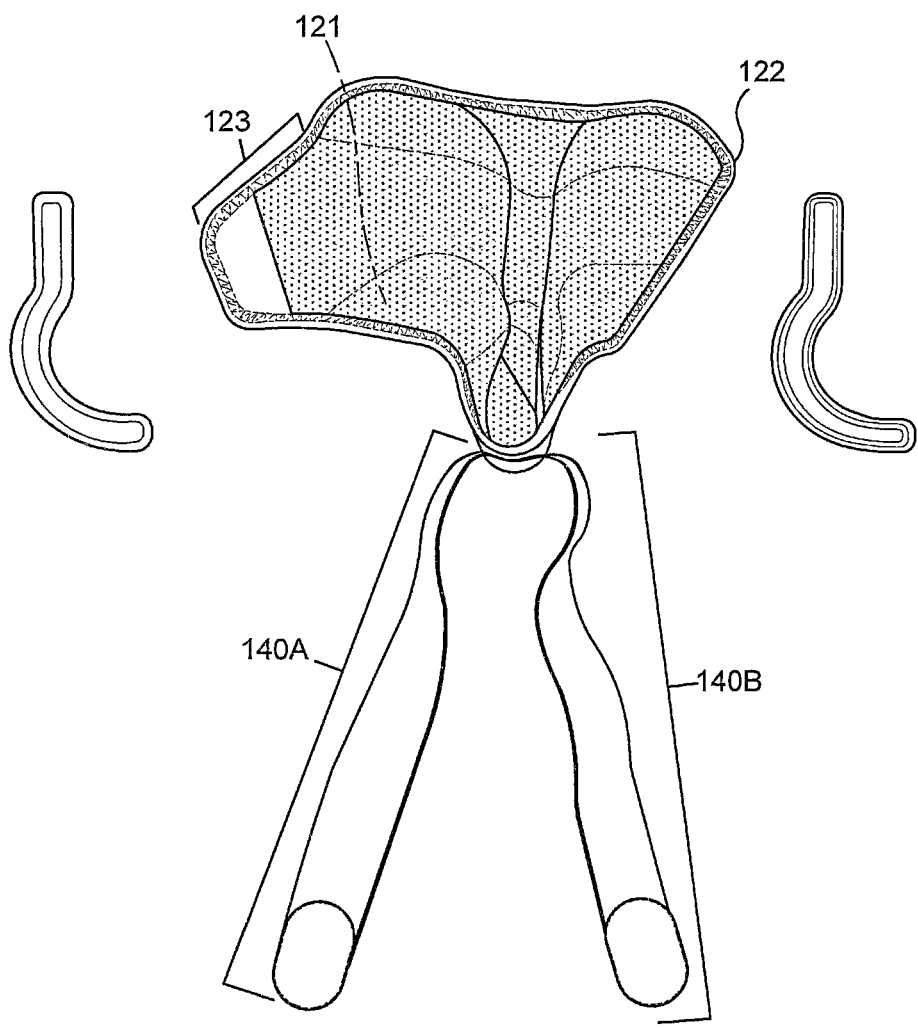
FIG. 14 is a rear view showing the first portion and second portion of the cuff after being separated, and showing the circumferential portion of the ankle stabilizer brace that is configured to be received upon the foot of the wearer.
Figure 14A:
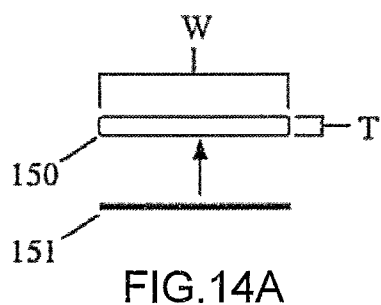
FIGS. 14A-14B show a first embodiment for forming the stays where hook or loop materials are secured to one side of the stay.

As seen in FIG. 14A, each of the medial stay 160 and lateral stay 170 may be formed of a reinforcement member 150 having a thickness T, and a width W. The material used for the reinforcement member 150 may include, but is not limited to, wood (e.g., alder, Douglas fir . . . ), metal (e.g., aluminum . . . ), plastic (e.g., low density polyethylene . . . ), composites (e.g., a glass fiber reinforced polymer . . . ), etc. In one embodiment, the thickness T of the reinforcement member 150 may be between 0.07 and 0.1 inches, and in another embodiment, the thickness T of the reinforcement member 150 may be between 0.1 and 0.15 inches, which thickness may depend upon the strength properties of the particular material utilized, and may be proportional to the size of the wrap 110 (i.e., the reinforcement member may be proportionately thicker for the ankle stabilizer brace that is sized to fit the foot and leg of a 6' tall 250 pound man that wears a size 12% shoe, than when formed and used for a four foot tall child that weighs 50 pounds and wears a size 5 shoe). Such thickness for the reinforcement member 150 may provide for lateral flexure of one end of the medial stay 160 and lateral stay 170 of about 0.1 to 0.2 inches when supported at its opposite end and its midpoint. The lateral flexure may accommodate substantially continuous attachment of the stays to the wrap 110 so that it may follow the contours of the wearer's foot, and may permit use of the same stay for the medial and lateral sides. The width W of each of the medial stay 160 and lateral stay 170 is necessarily a small arc-segment of the circumference of the leg that in enveloped by the wrap 110. Therefore the width W of each stay is preferably between 0.35 inches and 0.65 inches, and is more preferably between 0.40 inches and 0.6 inches, and most preferably between 0.45 inches and 0.55 inches so that the strap 140 may wrap properly around the stays and secure the stays to the wrap 110 that may curve around the wearer's leg and foot.

Figure 14B:
Figure 14C:
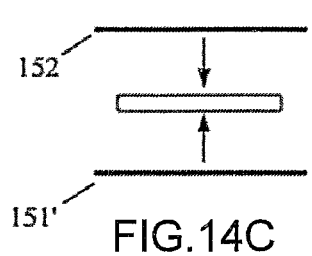
FIGS. 14C-14D show a second embodiment for forming the stays where hook and loop materials are secured to first and second sides of the stay, respectively.
Figure 14D:
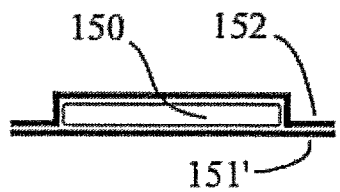
Figure 18:
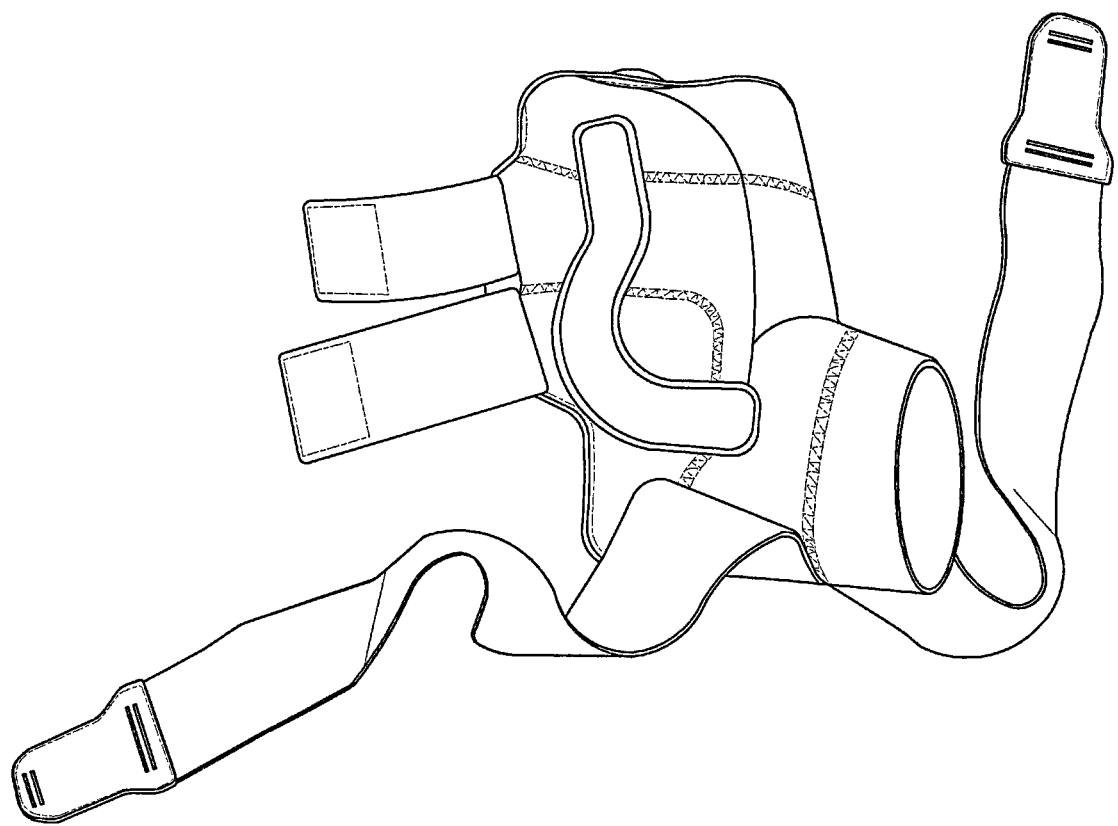
FIG. 18 is a side perspective view of the ankle stabilizer brace of FIG. 15, shown with its first and second strap portions separated from each other after detaching of the pair of rear straps, and with the first and second portions of the cuff after being separated.
Figure 19:
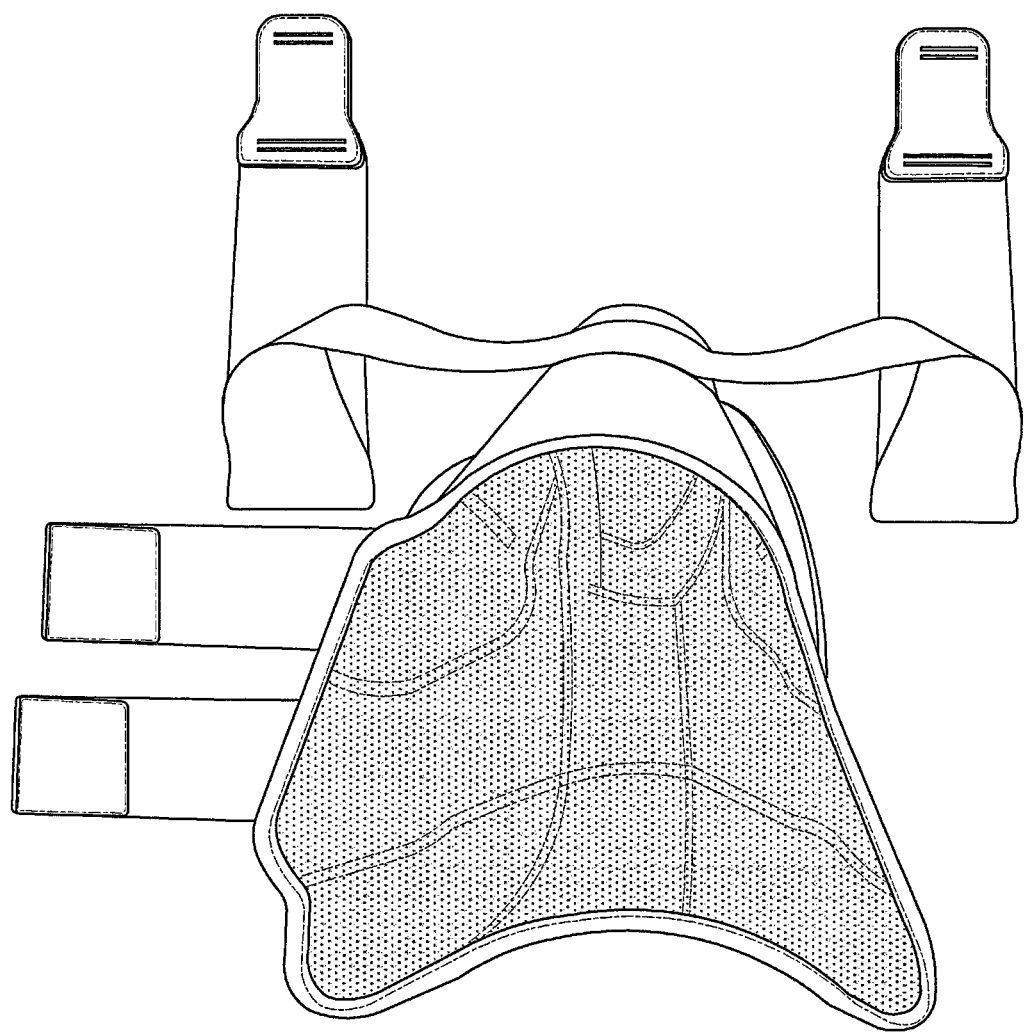
FIG. 19 is a top perspective view of the ankle stabilizer brace as seen in FIG. 18.
Figure 20:
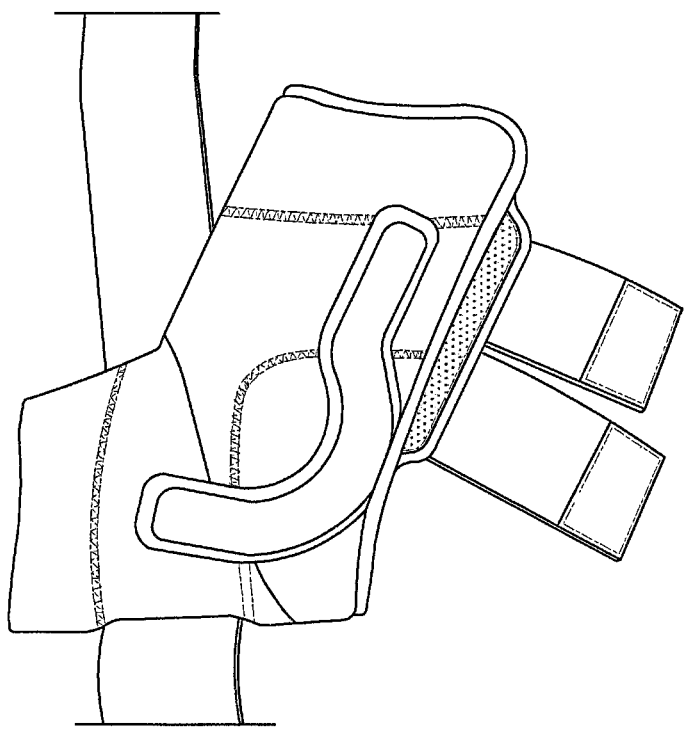
FIG. 20 is a left side view of the ankle stabilizer brace as seen in FIG. 18.
Figure 21:
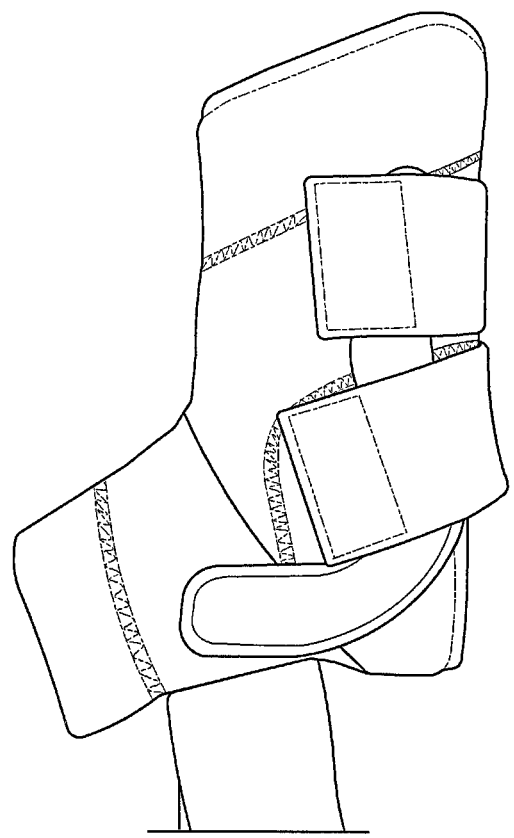
FIG. 21 is the left side view of FIG. 20, but shown with the rear straps attached to join the first and second strap portions together.

The attachment of each of the medial stay 160 and lateral stay 170 to the wrap 110 may be accomplished in any suitable manner, including, but not limited to: being fixedly attached thereto using adhesive, or by being overlaid by a cover material having a similarly shaped periphery that may be stitched to the wrap, or by being received in a pocket formed in the warp, etc. In a preferred embodiment, as be understood from FIGS. 14A-14B, each of the medial stay 160 and lateral stay 170 may have at least a patch 151 of the aforementioned hook material fixedly secured (e.g., by adhesive) to at least a portion of the entirety of one side of its reinforcement member 150, which patch of hook material may then be releasably secured to the wrap. To use the same stay for both the medial and lateral sides, the hook material can be applied to both the first and second sides of the reinforcement member 150. However, for ease of handling, and for other attachments scenarios described hereinafter, the reinforcement member 150 may alternatively have a patch 151' of hook material fixedly secured to the entirety of a first side that overhangs slightly beyond the periphery of the reinforcing member, and may also have a patch of loop material 152 also be fixedly secured to the entirety of the second side of the reinforcement member and be secured to the overhanging portion of the patch 151', as shown in FIGS. 14C-14D. The overhanging portions may help the wearer to grasp the stay to remove and adjust the placement of the medial stay 160 and lateral stay 170 on the wrap 110, as discussed hereinafter. Also, being so formed, the stays would necessarily only be capable of used on one side of the wrap 110 that has its exterior formed with a loop material, and may also be referred to the left and right stays rather than medial and lateral stays, although the use of medial and lateral is nonetheless used hereinafter for consistency. However, note the use in the figures of "L" (FIG. 9) and "R" (FIG. 10) on the two stays to indicate their respective use on the left side and right side of the wrap 110.

Figure 12:
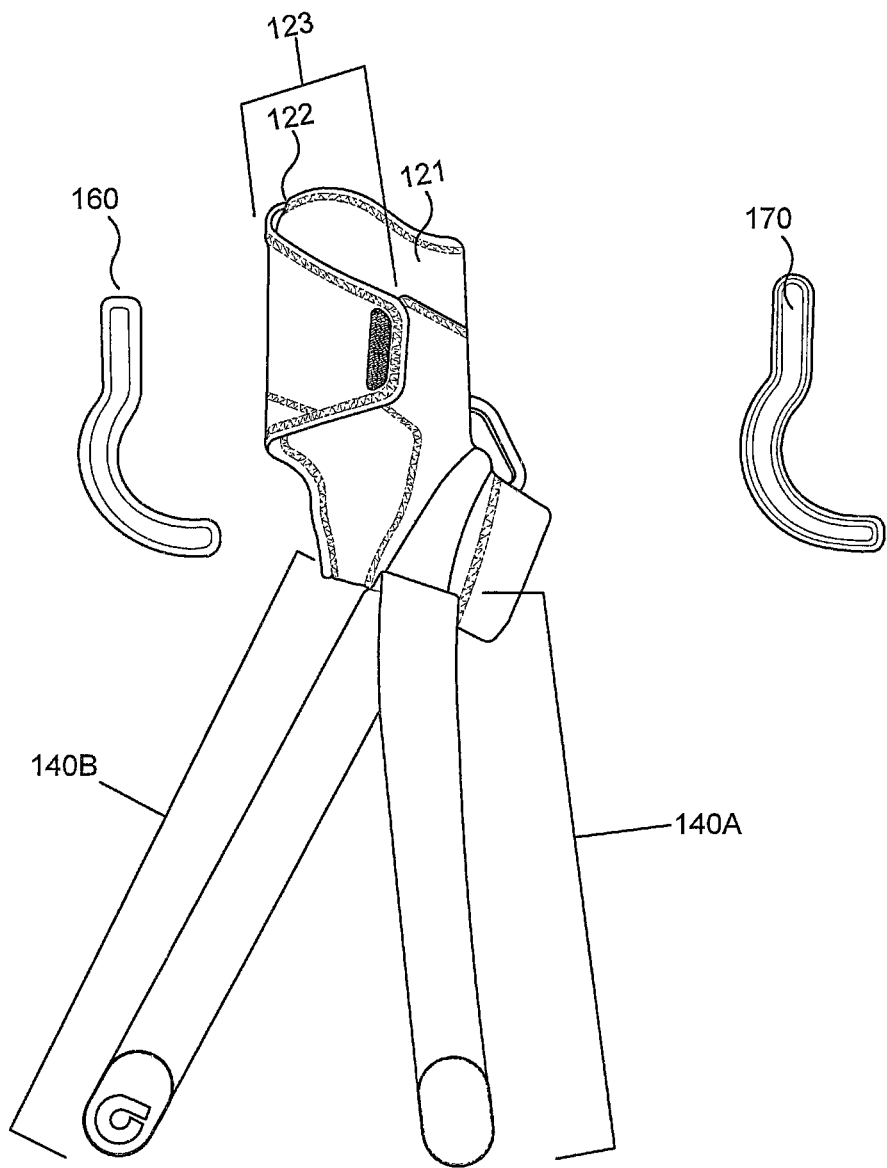
FIG. 12 is the right side view of FIG. 11, but showing the second particularly shaped stay after being detached from the right side of the ankle stabilizer brace.

The ankle stabilizer brace 101 may be formed with a first strap portion 140A and a second strap portion 140B that may be secured to the bottom of the foot portion 130, as shown in FIG. 12 and FIG. 14. In one embodiment, the first strap portion 140A and second strap portion 140B may be separate straps that are each individually secured to the bottom of the foot portion 130. In another embodiment, as may best be seen in FIG. 10, the first strap portion 140A and second strap portion 140B may be formed into a single unitary strap member 140, having a first end 141, and a second end 142, and may be secured to the wrap at a substantially central position between the first end and the second end. For a midsized ankle stabilizer brace 101 the single unitary strap member 140 may be roughly 36 inches long, for each side (140A/140B) to be able to wrap around the leg portion 120 and foot portion 130 a total of three times in a respective first direction and second direction, and then be secured to the wrap 110, and/or the stay.

To simplify and guide the wrapping procedure for the wearer, the ankle stabilizer brace 101 may also be formed to include one or two additional features.

Figure 8:
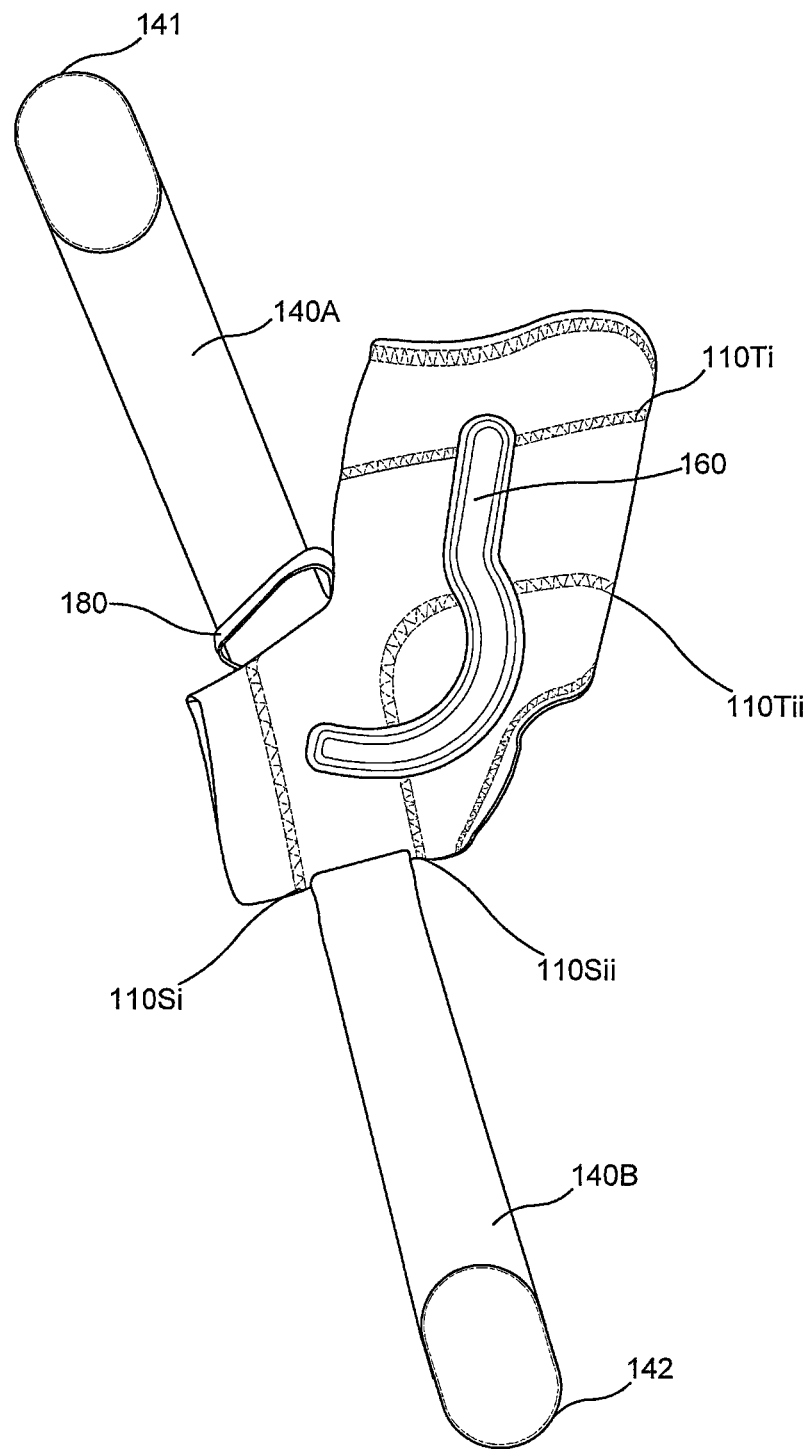
FIG. 8 is the left side view of FIG. 7, but showing the first strap portion after being removed from the support loop and unwound away from the left side of the ankle stabilizer brace, and stretched outwardly therefrom to completely expose a first particularly shaped stay.
Figure 9:
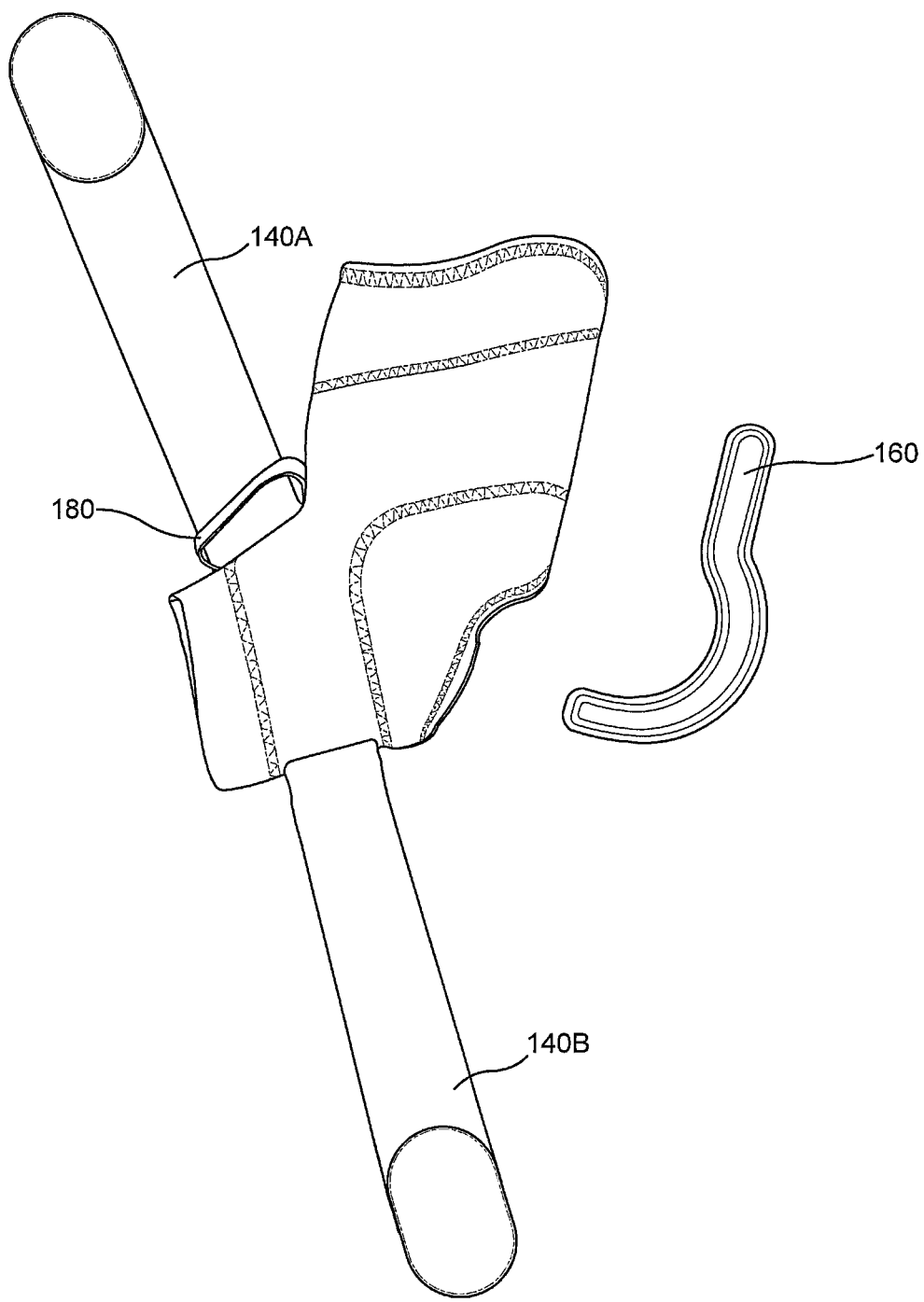
FIG. 9 is the left side view of FIG. 8, but showing the first particularly shaped stay after being detached from the left side of the ankle stabilizer brace.
Figure 13:
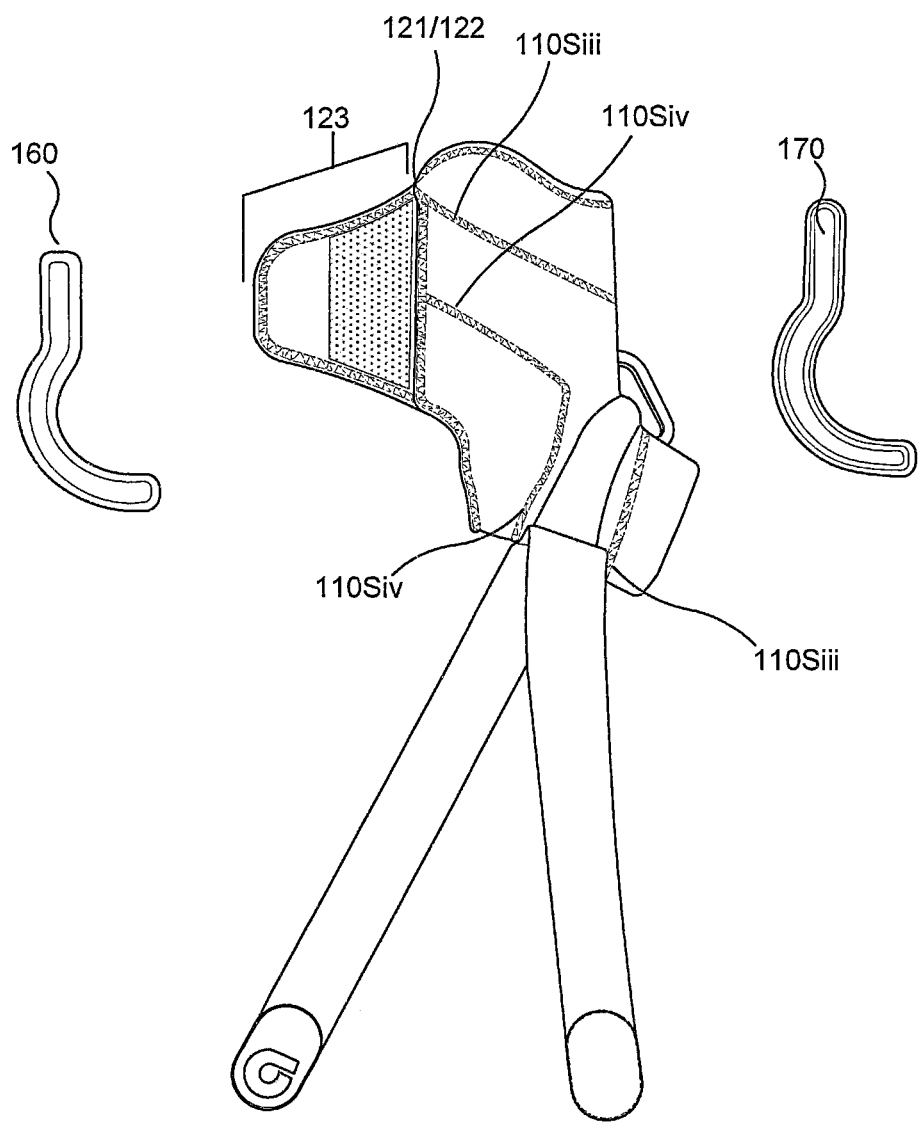
FIG. 13 is the right side view of FIG. 12, showing the first portion and second portion of the cuff that are configured to be secured about the wearer's leg above the ankle but after being separated from each other.

First, the wrap 110 may be formed to include particular markings configured to delineate a wrapping path for each of the first and second strap portions 140A/140B in each of said first and second directions. The markings may include, but is not limited to: a different color material sewn thereto, an applied ink, etc. In one embodiment, the particular marking may be stitching (e.g., a zig-zap stitch) that may also be a different color. For example, as seen in FIG. 8 and FIG. 13, the wrap 110 may have stitching 110Si and 110Sii to provide a wrapping path around the left side of the foot portion 130, and stitching 110Sii and 110Siv to provide a wrapping path around the right side of the foot portion 130. Also, as seen in FIG. 8 and FIG. 13, the wrap 110 may have stitching 110Siii and 110Siv to provide a wrapping path around the left side of the leg portion 120, and stitching 110Siii and 110Siv to provide a wrapping path around the right side of the leg portion 120.

Second, the ankle stabilizer brace 101 may be formed to have a loop 180 (see FIG. 9), which may be elastic, and which may be secured to the foot portion 130 of the wrap 110. The loop 180 may be configured (e.g., may have a width of sufficient size) to receive and to initially support the first and second strap portions 140A/140B as they are initially wound about the foot and leg.

Figure 7:
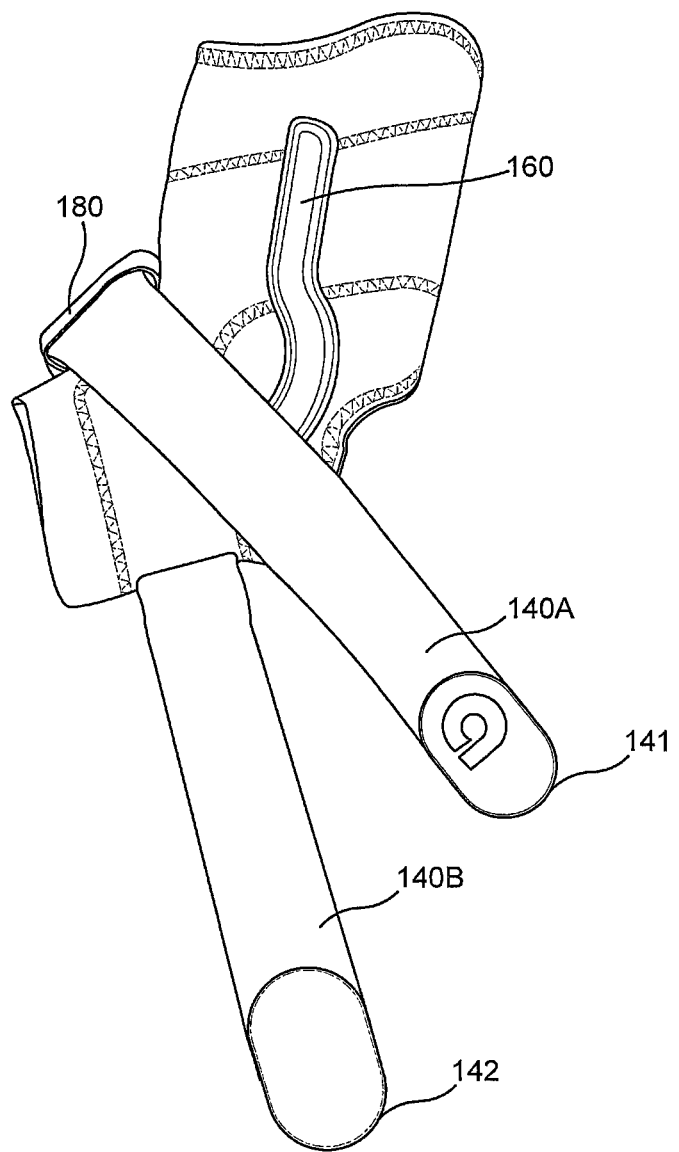
FIG. 7 is the left side view of FIG. 6, but showing the end of a second strap portion after being removed from the support loop and unwound away from the left side of the ankle stabilizer brace, and stretched outwardly therefrom.

Before the winding and securing process begins for the first and second strap portions 140A/140B, the The start of the winding and securing process may be seen in transitioning from the unattached/unwound positions for both the first and second strap portions 140A/140B, as shown in FIG. 8, to where the first strap portion 140A is wrapped around the right side of the foot portion 130, passed through the loop 180, and wrapped around the left side of the left side of the foot portion 130, as shown in FIG. 7. (Note that the wrapping process may alternatively begin with the second strap portion 140B).

Figure 4:
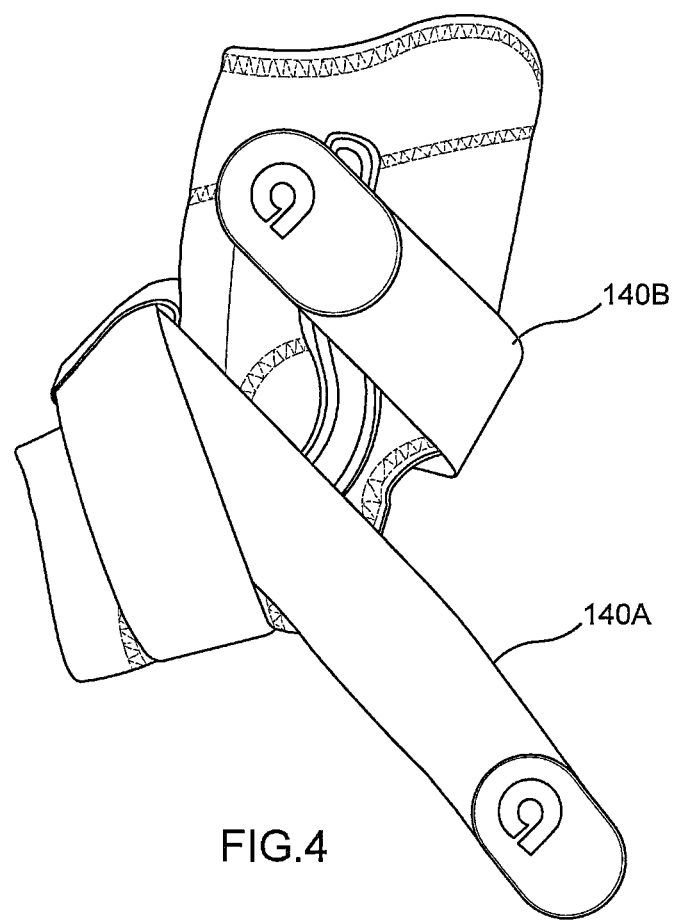
FIG. 4 is the ankle stabilizer brace of FIG. 3 with the end of the first strap portion detached, but as seen from the left side.
Figures 5, 6:
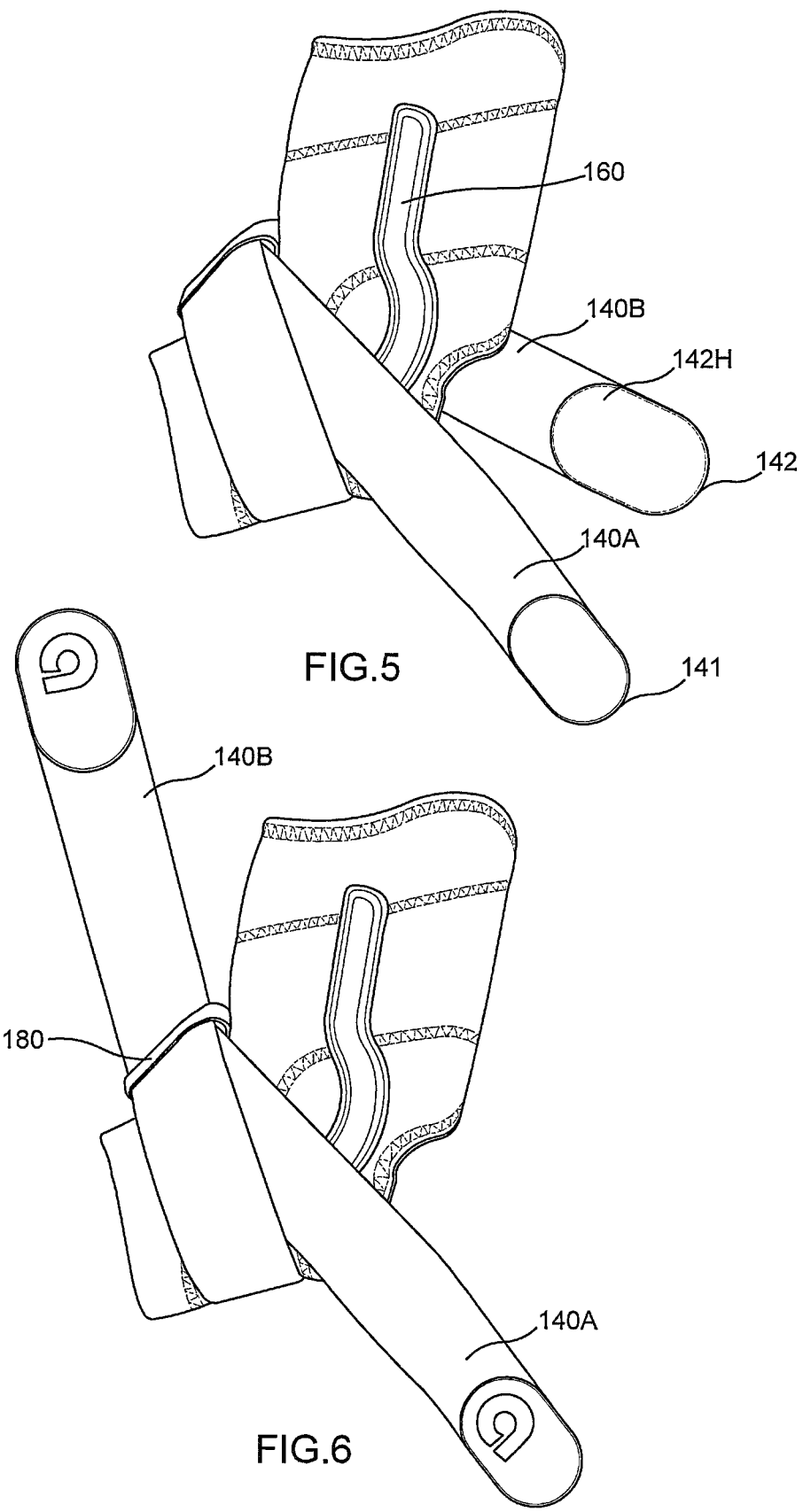
FIG. 5 is the left side view of FIG. 4, but showing an end of a second strap portion after being detached from the left side of the ankle stabilizer brace.
FIG. 6 is the left side view of FIG. 5, but showing the end of the second strap portion after being unwound away from the right side of the ankle stabilizer brace, and stretched outwardly therefrom.

Next, as may be seen in transitioning from FIG. 7 to FIGS. 6 and 5, the second strap portion 140B is wrapped around the left side of the foot portion 130 and passed through the loop 180 (FIG. 6), and then wrapped around the right side of the foot portion 130 (FIG. 5). Then the second end 142 of the second strap portion 140B is once again wrapped around the left side of the foot portion 130 and secured thereto using a patch of hook material 142H that is fixedly secured to the strap portion and which releasable secures that strap portion to the loop material on the exterior of the wrap 110 (FIG. 4). Lastly, the first end 141 of the first strap portion 140A is once again wrapped around onto the right side of the foot portion 130 and secured thereto using a patch of hook material 141H that is fixedly secured to the strap portion and which releasable secures that strap portion to the loop material on the exterior of the wrap 110 (FIG. 4).

Therefore, as just described, the first strap portion 140A is configured to wrap around the left side of the foot and over a top of the foot in the first direction, around the back of the leg, and wrap onto the right side with the first end being releasably secured thereat to overlay and secure the stay on the right side twice, and the stay on the left side once, while the second strap portion 140B is configured to wrap around the right side of the foot and over a top of the foot in the second direction, around the back of the leg, and wrap onto the left side with the second end being releasably secured thereat to overlay and secure the stay on the left side twice, and the stay on the right side once. Thus, each of the stays is overlaid and thereby secondarily supported in place (apart from the hook and loop materials of the stays and wrap) by the strap portions passing over each stay three times at three different locations, and also releasably protects the stay from inadvertent detachment by being caught on something as the wearer moves around. The arrangement also permit easy adjustment to the tightness of the straps, and also to the location of the stays which may be relocated and adjusted as needed for a particular wearer simply by removing the strap portions and repositioning the stays.

FIGS. 15-31 illustrate a stabilizer brace 201 that is formed substantially the same as brace 101, with a couple exceptions. In particular, and of most importance, it may utilize stay 26 and 270 FIGS. 24 and 25) that are pre-formed with contours to correspond to the contours of the foot at the locations at which it is to be mounted to the wrap. The contours may be generalized, or the stays may be custom formed by acquiring the wearer's exact foot/leg contours via imaging, or by using molds.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. An ankle brace configured to support and protect an ankle of a wearer against injury by inhibiting motion between a foot and lower leg of the wearer, said ankle brace comprising:
   a wrap, said wrap being formed of a flexible material and comprising: a first portion and second portion, said first portion configured to transition into said second portion; said first portion configured to envelop at least a portion of the foot of the wearer, and said second portion configured to envelop at least a portion of the lower leg of the wearer and to extend distally along the lower leg over the ankle;
   a lateral stay formed to have a selectively-shaped periphery configured to extend along a portion of the lower leg, around the ankle, and along a lateral portion of the foot of the wearer;
   a medial stay formed to have a selectively-shaped periphery configured to extend along a portion of the lower leg, around the ankle, and along a medial portion of the foot of the wearer;
   wherein said selectively shaped periphery of each of said lateral and medial stays comprises:
      a first substantially straight portion configured to overlie the tibia and fibula bones of the wearer;
      a first curved portion configured to curve back towards the rear of the wearer's foot when said ankle brace is worn;
      a second curved portion configured to curve around the rear and lower sides of the wearer's ankle; and
      a second substantially straight portion configured to extend from said second curved portion at the lower side of the wearer's ankle along a portion of the wearer's foot directly toward the toes;
   wherein said lateral and medial stays are configured for respective attachment to lateral and medial sides of said wrap; and wherein said lateral and medial stays are each rigid about a first respective axis, to inhibit relative motion between the foot and lower leg of the wearer to inhibit foot dorsiflexion;
   wherein each of said lateral and medial stays comprise a constant cross-sectional shape; and
   a first strap portion and a second strap portion secured to said wrap; said first strap portion configured to be wound about and releasably secure to said wrap in a first direction; and said second strap portion configured to be wound about and releasably secure to said wrap in a second direction.

2. The ankle brace according to claim 1,
   wherein said first strap portion is configured to wrap around a top of the foot in the first direction, around the back of the leg, and terminate with releasable securement proximate to either of said lateral or medial sides of said wrap;
   wherein said second strap portion is configured to wrap around a top of the foot in the second direction, around the back of the leg, and terminate with releasable securement proximate to the other of said lateral or medial sides of said wrap; and
   wherein said medial stay is thereby overlaid by said first and second strap portions at three locations to redundantly secure said medial stay to said wrap, and wherein said lateral stay is thereby overlaid by said first and second strap portions at three locations to redundantly secure said lateral stay to said wrap.

3. The ankle brace according to claim 2 wherein said lateral and medial stays are configured for respective attachment to lateral and medial sides of said wrap using hook and loop materials on said wrap and on a lateral side of said medial stay and on a medial side of said lateral stay.

4. The ankle brace according to claim 3,
   wherein each of said first and second strap portions are formed of a flexible material that is slightly elastic, said slightly elastic material comprising a maximum percent elongation of between 2 percent and 5 percent;
   wherein said medial side of said medial stay and said lateral side of said lateral stay are configured for respective attachment to said first and second strap portions using hook and loop materials on a distal end of said first and second strap portions, and on a medial side of said medial stay and on a lateral side of said lateral stay; and
   wherein each of said distal ends of said first and second strap portions are securable to each of said wrap and said medial and lateral stays, to thereby adjust a tension in each of said first and second strap portions.

5. The ankle brace according to claim 4 wherein said first strap portion and said second strap portion are formed as a single unitary strap having a first end and a second end, and being secured to said wrap at a central position between said first end and said second end of said single unitary strap.

6. The ankle brace according to claim 5 wherein said single unitary strap is secured to said first portion of said wrap, proximate to a center bottom of said first portion of said wrap, being thereby configured to be secured proximate to a center bottom of the wearer's foot.

7. The ankle brace according to claim 6 further comprising stitching configured to delineate a wrapping path for said strap on each of said first and second portions of said wrap, in each of said first and second directions.

8. The ankle brace according to claim 7 further comprising an elastic loop secured to a center top of said first portion of said wrap, to thereby position said loop to provide support for each of said first and second strap portions proximate to the top of the wearer's foot.

9. The ankle brace according to claim 8 wherein said second portion comprises first and second sides configured to wrap around the lower leg of the wearer and be releasably secured together using hook and loop materials.

10. The ankle brace according to claim 9
   wherein each of said lateral stay and said medial stay are flat.

11. The ankle brace according to claim 9,
   wherein said lateral stay comprises contours to correspond to a contour of the lateral side of the foot, ankle, and lower leg;
   wherein said medial stay comprises contours to correspond to a medial side of the foot, ankle, and lower leg.

\* \* \* \* \*